(12) United States Patent
Davis

(10) Patent No.: US 7,561,271 B2
(45) Date of Patent: Jul. 14, 2009

(54) SOURCE ADJUSTED COLORIMETER

(76) Inventor: James E. Davis, 26 Austin Rd., Wilmington, DE (US) 19810-2203

(*) Notice: Subject to any disclaimer, the term of this patent is extended or adjusted under 35 U.S.C. 154(b) by 0 days.

(21) Appl. No.: 11/981,418

(22) Filed: Nov. 1, 2007

(65) Prior Publication Data
US 2009/0116016 A1 May 7, 2009

(51) Int. Cl.
*G01J 3/51* (2006.01)
(52) U.S. Cl. .................. 356/402; 356/411; 356/414; 356/416; 356/425
(58) Field of Classification Search .............. 356/402, 356/425
See application file for complete search history.

(56) References Cited
U.S. PATENT DOCUMENTS

| | | | |
|---|---|---|---|
| 1,535,070 A | 4/1925 | Klett | |
| 1,961,913 A | 6/1934 | Reynolds | |
| 2,042,281 A | 5/1936 | Traver | |
| 2,555,744 A * | 6/1951 | Harvey et al. | 356/425 |
| 2,561,243 A * | 7/1951 | Sweet | 356/435 |
| 3,332,313 A * | 7/1967 | Batson | 356/408 |
| 4,305,659 A * | 12/1981 | Bilstad et al. | 356/40 |

* cited by examiner

*Primary Examiner*—F. L Evans

(57) ABSTRACT

A low cost calorimeter wherein a linear taper potentiometer proportions the current through sample and reference solid state light sources in a near logarithmic fashion. The position of the potentiometer slider is proportional to the absorbance of the solution in the sample path when the light intensity of the two paths is balanced. The light intensity may be balanced visually or with a simple electronic comparator.

9 Claims, 2 Drawing Sheets

US 7,561,271 B2

SOURCE ADJUSTED COLORIMETER

CROSS-REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

This invention relates generally to a calorimeter and in particular to a simple and low cost calorimeter with simultaneously adjusted sample and reference light sources.

BACKGROUND OF THE INVENTION

Manually balanced calorimeters of the Dubosc type have been known for more than a century. The generally large sample size and costly precision construction has lead to alternate colorimeters, generally shifting to electronic photo detection with analog logarithmic conversion of optical transmission (intensity) into absorbance or to microcomputers providing algorithmic conversion into absorbance.

U.S. Pat. No. 1,961,913 teaches a calorimeter for measuring the color or intensity of light reflected from a piece of material. A resistor (rheostat) is associated with a comparison incandescent light and includes a color indicating dial. The resistor varies the light intensity of the comparison incandescent light until a galvanometer reads the same as an incandescent light illuminating the sample. It is not clear how the intensity may be measured and at other times the color is measured. The colorimeter is not a pyrometer where the color of the filament is matched to the sample color temperature. There is no teaching of reading absorbance.

U.S. Pat. No. 2,042,281 teaches a moving a source of light along a rail until a sample and a reference photoelectric cell generate equal current as indicated by a galvanometer. An intensity scale associated with the position of the source of light can be determined by the inverse square law. The calorimeter is large and requires precision mechanical components.

There remains a need for a low cost calorimeter with a minimum of precision electronic components or microcomputers or precision mechanical components.

There also remains a need for a portable and rugged calorimeter.

SUMMARY OF THE INVENTION

The invention is directed to a colorimeter comprising a first and a second solid-state light source, a first potentiometer having a first end attached to the first solid-state light source and a second end attached to the second solid-state light source and a slider attached to an electric power source, a light comparator for matching the intensity of the first and second light sources, a first light path conducting light from the first solid-state light source through a sample to the light comparator, a second light path conducting light from the second solid-state light source to the light comparator, wherein the position of the slider is proportional to the sample absorbance.

The solid state light sources may be light emitting diodes (LEDs).

The LEDs may be white and the wavelength or color selected by an optical color filter.

The reference beam also may be directed though the sample.

The zero point of the scale may be adjusted with a "zero" potentiometer.

The absorbance range of the scale may be adjusted with a "range" potentiometer.

The balance of the sample and reference beams may be detected by visual comparison using well known techniques.

Alternatively the balance of the sample and reference beams may be detected by photoelectric comparator. The balance may be indicated by two LED indicators indicating whether the potentiometer is above, at, or below balance. A photoelectric comparator is useful for operators with color blindness and also in reducing operator subjectivity.

Photodetectors in the photoelectric comparator may be phototransistors.

DETAILED DESCRIPTION

A novel comparison calorimeter that is low cost and portable utilizes a linear taper potentiometer to proportion current through two solid state light sources, such as light emitting diodes (LEDs). The position of the potentiometer slider is proportional to the absorbance of the solution in the sample path when the light intensities of the two paths are balanced. The light intensities may be balanced visually or with simple electronic comparison.

Figure 1:
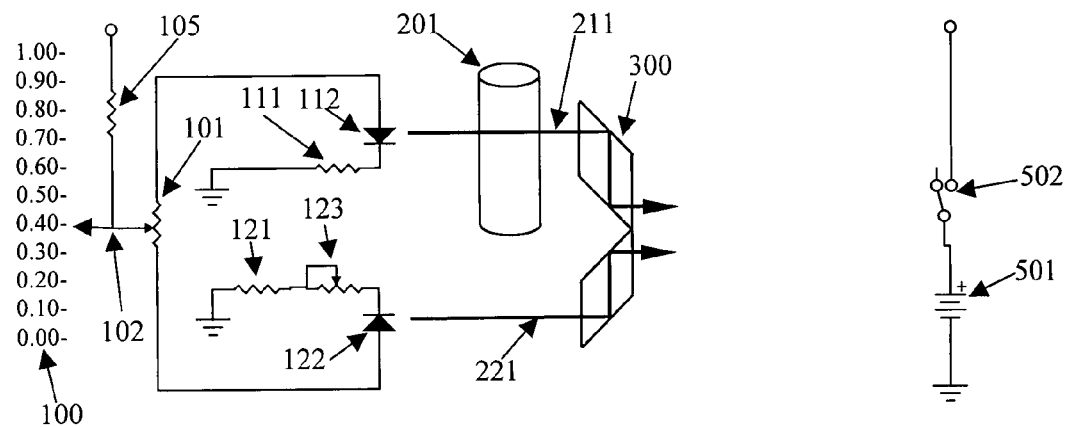
FIG. 1 is a schematic of a visual comparison calorimeter.

FIG. 1 is a schematic of the visual comparison calorimeter wherein a linear taper first potentiometer, 101, with a manual slider and scale pointer, 102. The slider is electrically connected through a current limiting resistor, 105, to an electric power source, such as a voltage supply buss indicated by the open circle. A scale, 100, is calibrated in absorbance or concentration units. Resistor 111 limits the current through the sample or first LED, 112, and resistor 121 and trimmer resistor 123 limit the current through the reference or second LED, 122. The resistors 111 and 121 and trimmer resistor 123 determine the offset and range of absorbance. A scale, 100, pointed to by the slider, 102, directly indicates the absorbance or sample concentration. The sample container, 201, may be a simple test tube or cuvette. A first light path, 211, conducts light from the first solid-state light source through a sample to the light comparator, 300. A second light path, 221, conducts light from the second solid-state light source to the light comparator, 300. The visual light comparator, 300, can be of many known forms. For example, without limitation, U.S. Pat. No. 1,535,070 to Klett illustrates a visual comparator.

Figure 2:
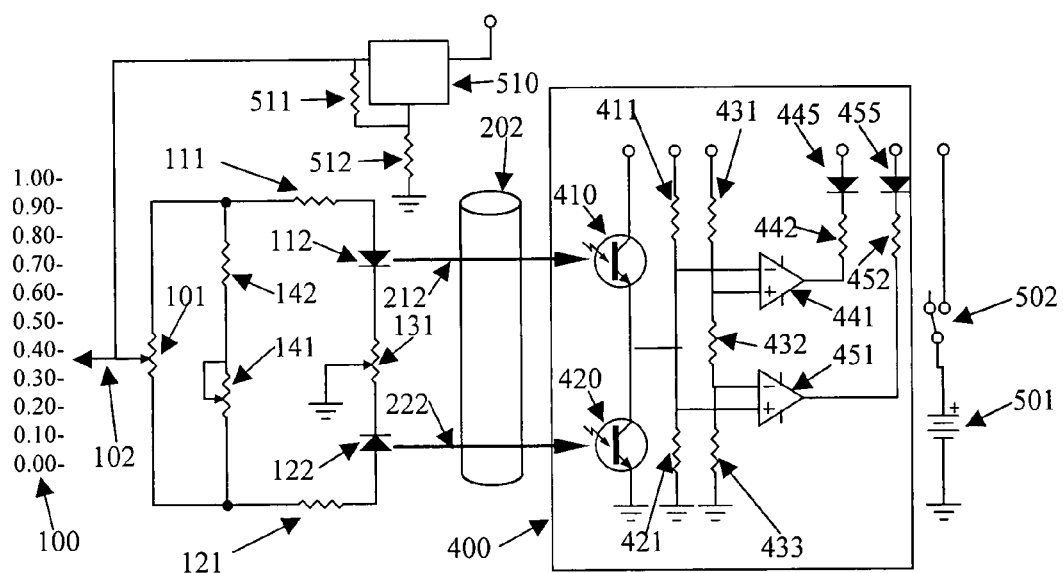
FIG. 2 is a schematic of an enhanced colorimeter having zero and range adjustments and photoelectric comparison with LED balance indicators.

FIG. 2 is a schematic of an enhanced calorimeter having zero and. range adjustments and photoelectric comparison with LED balance indicators. Elements common with FIG. 1 have the same numeric identifier. Rather than connection to current limiting resistor, 105, the slider, 101, is connected to a voltage regulator, 510, to further stabilize the absorbance as indicated by the slider, 102, and also to limit the current through the LEDs. Resistors 511 and 512 set the regulated voltage applied to the slider, 102. A first light path, 212, and a second light path, 222, conduct light from the first and second solid-state light sources through an alternate sample container or cuvette, 202, to the photoelectric light comparator, 400. In this case the sample or first LED, 112, is of a different frequency or color than the reference or second LED, 122.

A "zero" potentiometer, 131, shifts the ratio of the currents through the first and second LEDs, 112 and 122. The current limiting resistors, 111 and 121, may be retained.

A "range" potentiometer, 141, and resistor, 142, trim the absorbance range of the first potentiometer, 101. This overcomes the wide tolerance in the value of commercial first potentiometers and allows matching of the scale to concentration values of different chemistries.

The light from the sample or first light path, 212, impinges on a first photodetector, 410, and light from the reference or second light path, 222, impinges on a second photodetector, 420. Preferred photodetectors are silicon phototransistors. The photodetectors are connected as part of a comparator bridge. Resistors, 411 and 421, set the sensitivity of balance. Resistors, 431, 432, and 433, set comparison voltages for the voltage comparators, 441 and 451. Voltage comparators, 441 and 451, may be part of a dual comparator such as the common LM317. Comparator 441 detects the slider above balance and turns on indicator LED 445 with current limited by resistor 442. Comparator 451 detects the slider below balance and turns on indicator LED 455 with current limited by resistor 452. Both indicator LEDs are on in the balance condition.

A motor may be connected to the comparator and to the slider of the first potentiometer to automatically drive the first potentiometer to a balance condition. A signal from the comparator indicating the slider is above balance causes the motor to drive the slider downward until the comparator detects balance. Similarly for the slide below balance. Such servo control means are well known in the art.

Figure 3:
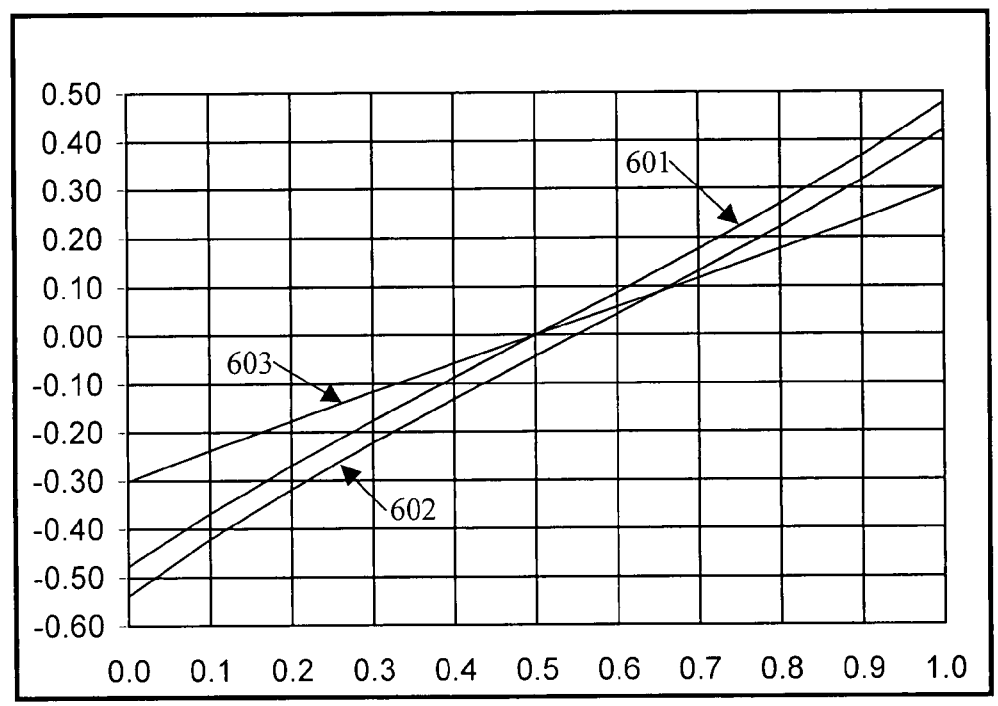
FIG. 3 is a graph of the ratio of LED currents vs. potentiometer setting and the effects of zero and range potentiometers.

FIG. 3 is a graph of the logarithm of the ratio of LED currents vs. potentiometer slider position and the effect of zero and range potentiometers. Curve 601 shows the calculated logarithm (base 10) of the ratio of the currents through the sample and reference LEDs. The curve is substantially linear over the range −0.5 to +0.5. By reducing the value of the current limiting resistors, 111 and 121, the range may be expanded beyond one log unit, however curvature or deviation from conformance to a logarithm becomes apparent. Such curvature may be useful in creating an expanded range in conjunction with a nonlinear scale, particularly at absorbances greater than one.

Curve 602 illustrates the effect of curve displacement by the "zero" potentiometer, 131. Curve 603 illustrates the effect of a decreased range (higher sensitivity) by the "range" potentiometer, 141.

The "zero" potentiometer is best used in conjunction with a neutral density filter or aperture in the reference light path. A 0.5 absorbance filter will shift the zero position of the slider to correspond to zero absorbance in the sample path. The different LED efficiencies or color and differing frequency (color) sensitivity of the photodetector can also be compensated by selection of the neutral density filter.

Additional color filters may be placed in front of the photodetectors to reduce interference from light leakage from external sources or from scatter from the other light source when both light paths traverse the sample.

Figure 4:
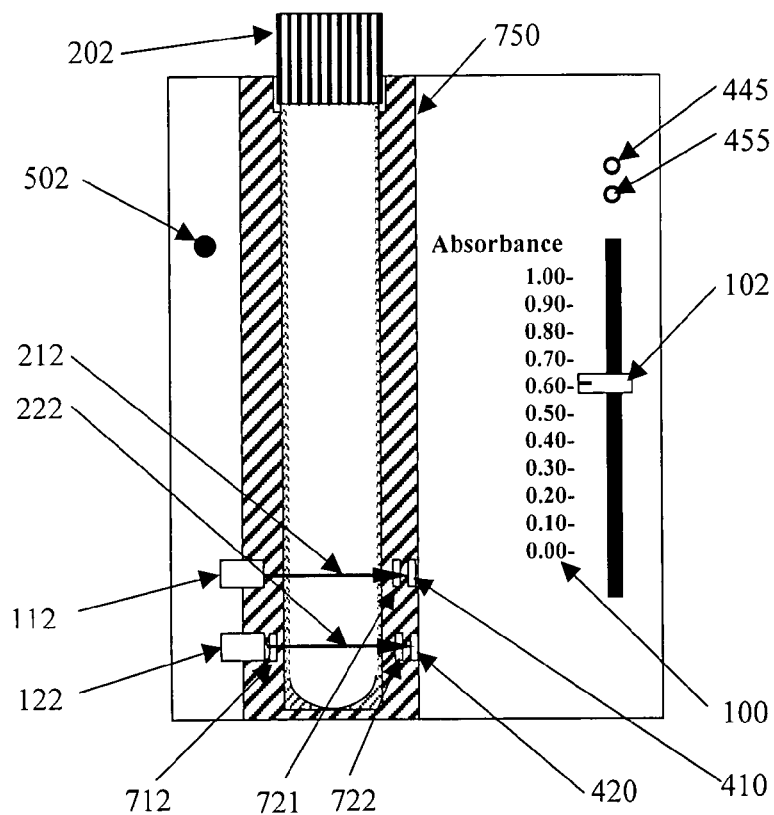
FIG. 4 is an elevation drawing of the calorimeter with a partial cutaway of the sample container and optical path.

FIG. 4 is an elevation drawing of the colorimeter with a partial cutaway of the sample container, 202, and light paths, 212 and 222. Elements common with FIGS. 1 and 2 have the same numeric identifier. A sample holder, 750, holds the sample container, 202, in a fixed relation to the light paths. A neutral density filter, 712, approximately balances zero absorbance, that is, when water is in the sample container. The zero potentiometer, 131, finely balances the zero absorbance. Color filters, 721 and 722, may be used to reduce light leakage to the respective photo detectors, 410 and 420.

With the teachings of this invention, it will be apparent to those skilled in the art as to how to change the elements for different applications.

The invention claimed is:

1. A colorimeter comprising:
    a first and a second solid-state light source;
    a first potentiometer having a first end attached to the first solid-state light source and a second end attached to the second solid-state light source and a slider attached to an electric power source;
    a light comparator for matching the intensity of the first and second light sources;
    a first light path conducting light from the first solid-state light source through a sample to the light comparator;
    a second light path conducting light from the second solid-state light source to the light comparator;
    wherein the position of the slider is proportional to the sample absorbance.

2. The colorimeter of claim 1 wherein the first and second solid-state light sources comprise LEDs.

3. The colorimeter of claim 2 wherein the first LED comprises a white LED and an optical color filter.

4. The calorimeter of claim 2 wherein the second LED is a different color and the second light path is conducted through the sample.

5. The calorimeter of claim 1 additionally comprising a zero potentiometer for adjusting the zero absorbance position of the slider having a first end attached to the first solid-state light source and a second end attached to the second solid-state light source and a slider attached to electrical ground.

6. The calorimeter of claim 1 additionally comprising a range potentiometer for adjusting the absorbance range having a first end attached to the first end of the first potentiometer and a second end attached to the second end of the first potentiometer and a slider attached to the first end of the range potentiometer.

7. The colorimeter of claim 1 wherein the light comparator comprises a split screen for visual comparison.

8. The colorimeter of claim 1 wherein the light comparator comprises:
    a first and second photodetector for receiving light from the first and second light paths;
    a voltage comparator for indicating a photo current balance between the first and second photodetectors.

9. The colorimeter of claim 8 wherein the first and second photodetectors comprise phototransistors.

\* \* \* \* \*